US011395874B2

(12) United States Patent
Manwaring et al.

(10) Patent No.: US 11,395,874 B2
(45) Date of Patent: Jul. 26, 2022

(54) SEQUENTIAL COLLAPSE WAVEFORM DRESSING

(71) Applicant: KCI Licensing, Inc., San Antonio, TX (US)

(72) Inventors: Michael E. Manwaring, San Antonio, TX (US); Chester R. Edlund, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 977 days.

(21) Appl. No.: 16/072,739

(22) PCT Filed: Jan. 24, 2017

(86) PCT No.: PCT/US2017/014741
§ 371 (c)(1),
(2) Date: Jul. 25, 2018

(87) PCT Pub. No.: WO2017/132144
PCT Pub. Date: Aug. 3, 2017

(65) Prior Publication Data
US 2019/0030220 A1    Jan. 31, 2019

Related U.S. Application Data

(60) Provisional application No. 62/288,167, filed on Jan. 28, 2016.

(51) Int. Cl.
*A61M 1/00* (2006.01)
*A61F 13/00* (2006.01)
*A61F 13/02* (2006.01)

(52) U.S. Cl.
CPC ....... *A61M 1/962* (2021.05); *A61F 13/00068* (2013.01); *A61F 13/0203* (2013.01);
(Continued)

(58) Field of Classification Search
CPC .......... A61M 1/90; A61M 1/962; A61M 1/74; A61M 1/915; A61M 1/918; A61M 1/91;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for corresponding Application No. PCT/US2017/014741, dated Mar. 30, 2017.
(Continued)

*Primary Examiner* — Benjamin J Klein (57) ABSTRACT

An apparatus for tissue therapy may include a sequentially-collapsing tissue interface for use with negative pressure. The apparatus may include a first manifold and a second manifold fluidly coupled to the first manifold through a constricted fluid path. A fluid conductor may fluidly couple the second manifold to the first manifold. The fluid conductor may constrict fluid flow between the first manifold and the second manifold. The apparatus may include a negative-pressure source fluidly coupled to the first manifold in some embodiments. A controller may be configured to operate a negative-pressure source to provide negative pressure to a tissue interface in a therapy sequence adapted to propagate a wave in the tissue site. Such motion may be particularly advantageous or beneficial for a variety of conditions, including lymphedema, edema, or venous insufficiency.

5 Claims, 7 Drawing Sheets

(52) U.S. Cl.
CPC ............ *A61M 1/0001* (2013.01); *A61M 1/74* (2021.05); *A61M 1/75* (2021.05); *A61M 1/90* (2021.05)

(58) Field of Classification Search
CPC ............ A61F 13/0203; A61F 13/00068; A61F 13/0216
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,147,468 B2 * | 4/2012 | Barta | A61F 13/00034 604/313 |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0069829 A1 * | 3/2010 | Hutchinson | A61F 13/0203 604/28 |
| 2010/0125259 A1 | 5/2010 | Olson | |
| 2011/0009839 A1 | 1/2011 | Lu et al. | |
| 2012/0143114 A1 * | 6/2012 | Locke | A61L 15/16 602/43 |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |

(56) References Cited

FOREIGN PATENT DOCUMENTS

| | | |
|---|---|---|
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2013071253 A1 | 5/2013 |
| WO | 2014140608 A1 | 9/2014 |
| WO | 2015126702 A1 | 8/2015 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. ?uki?, Ž. Maksimovi?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.

* cited by examiner

SEQUENTIAL COLLAPSE WAVEFORM DRESSING

This application is the National Stage of International Application No. PCT/US2017/014741, entitled "Sequential Collapse Waveform Dressing," filed Jan. 24, 2017 and claims the benefit of U.S. Provisional Patent Application No. 62/288,167, entitled "Sequential Collapse Waveform Dressing," filed Jan. 28, 2016, all of which are incorporated herein by reference for all purposes.

TECHNICAL FIELD

The invention set forth in the appended claims relates generally to tissue treatment systems and more particularly, but without limitation, to negative pressure tissue treatment systems having sequentially connected dressing segments.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, new applications for negative-pressure therapy continue to evolve, and improvements to therapy systems, components, and processes may benefit healthcare providers and patients.

BRIEF SUMMARY

New and useful systems, apparatuses, and methods for tissue therapy in a negative-pressure environment are set forth in the appended claims. Illustrative embodiments are also provided to enable a person skilled in the art to make and use the claimed subject matter.

For example, in some embodiments, such an apparatus may comprise a sequentially-collapsing dressing for use with negative pressure. A rolling application of negative pressure through the dressing can induce a wave-like motion within underlying tissue, which can promote fluid propagation in some embodiments. Such motion may be particularly advantageous or beneficial for a variety of conditions, including lymphedema, edema, or venous insufficiency.

In more particular examples, a dressing may comprise a sequence of foam or other negative-pressure transmitting dressing segments connected by restrictive fluid communication points. In some embodiments, for example, negative-pressure transmitting segments may be coupled in sequence through tubes or other fluid conductors that can substantially reduce the flow of air from one segment to another. In operation, such a configuration can create a sequential drawdown of adjacent segments as negative-pressure therapy is initiated. A break or reduction in negative-pressure delivery can also provide an analogous sequential filling of adjacent segments with air. Additionally, some embodiments of dressing segments may comprise a tissue-contacting side having a patterned void space, which can be used to impart an elastic stretch on intact tissue. The pattern of void spaces may define features such as channels or ridges, for example, which can impart a peristaltic wave of elastic lift on skin or other tissue during negative-pressure drawdown, release, or both.

More generally, in some example embodiments, an apparatus for tissue therapy may include a first manifold and a second manifold fluidly coupled to the first manifold through a constricted fluid path. For example a fluid conductor, such as a tube, may fluidly couple the second manifold to the first manifold in some embodiments. The fluid conductor may be configured to constrict fluid flow between the first manifold and the second manifold. The apparatus may additionally comprise a negative-pressure source fluidly coupled or configured to be fluidly coupled to the first manifold in some embodiments. A negative-pressure source may provide or be configured to provide negative pressure to the first manifold for a drawdown interval and a release interval. In some configurations, the first manifold may include a manifold face having a void adapted to stretch tissue.

Other example embodiments may be a system for treating a tissue site. The system may include a negative-pressure source and at least two manifold segments. The manifold segments may be sequentially connected to the negative-pressure source. Each of the manifold segments may be attached to another of the manifold segments through a fluid conductor configured to constrict flow between the manifold segments. In some configurations, the system may additionally include a controller configured to operate the negative-pressure source for at least one of a drawdown interval, a release interval, and a holding interval. For example, the controller may be configured to operate the negative-pressure source in a sequence comprising a drawdown interval, a holding interval, and a release interval.

In yet other example embodiments, a method for treating a tissue site may include applying first and second manifolds to the tissue site. The method may also include applying negative pressure to the first manifold, which can be distributed to the second manifold through a constricted fluid path between the first manifold and the second manifold. In some configurations, negative pressure may be applied for a therapy sequence, which may include various combinations of a drawdown interval, a holding interval, and a release interval. A therapy sequence may be adapted to propagate a wave in the tissue site in some example applications.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
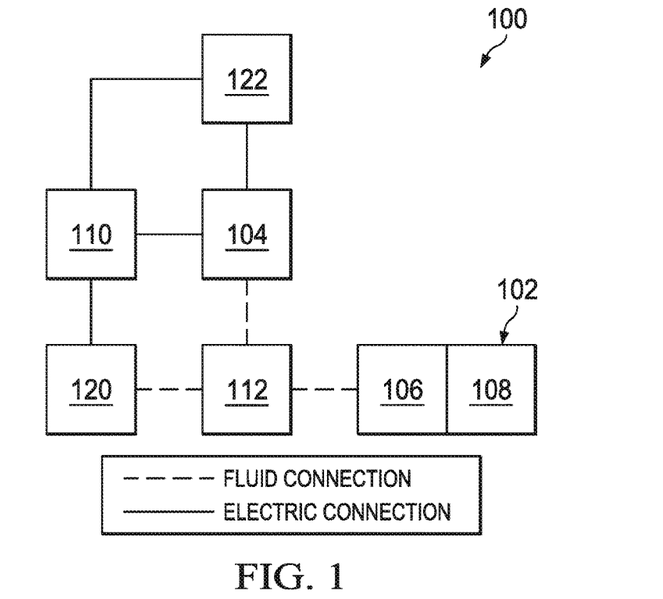
FIG. 1 is a functional block diagram of a therapy system constructed in accordance with the principles of the present disclosure.
Figure 2A:
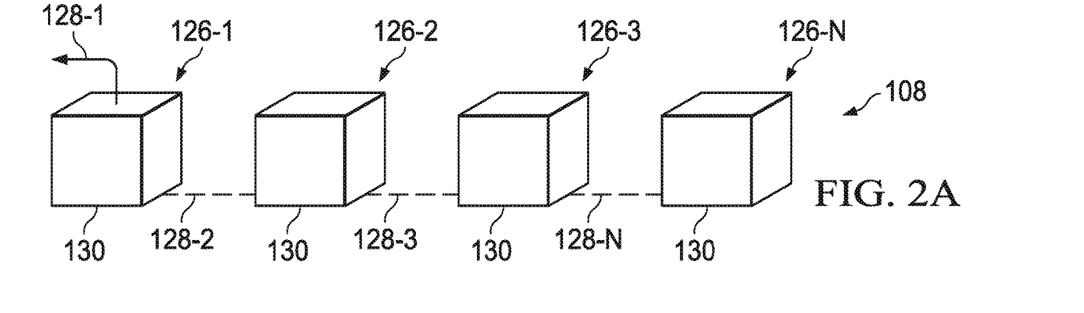
FIGS. 2A-2D are schematic diagrams of a tissue interface of the therapy system of FIG. 1.
Figure 2B:
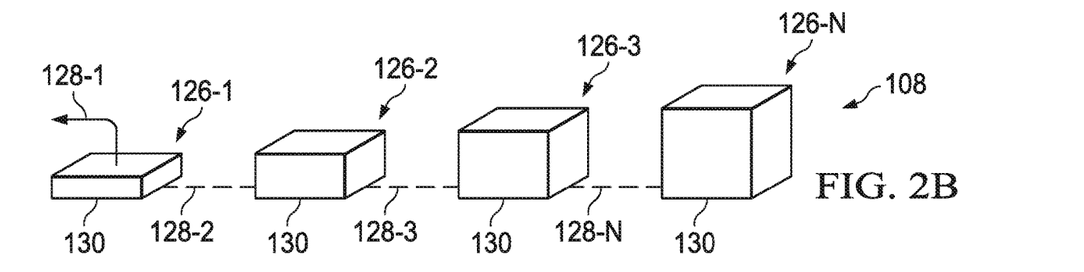
Figure 2C:
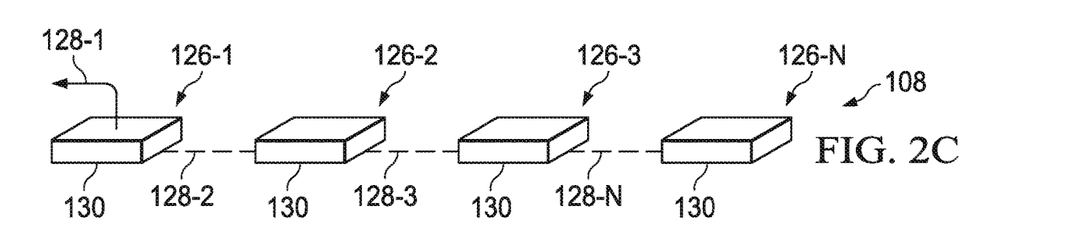
Figure 2D:
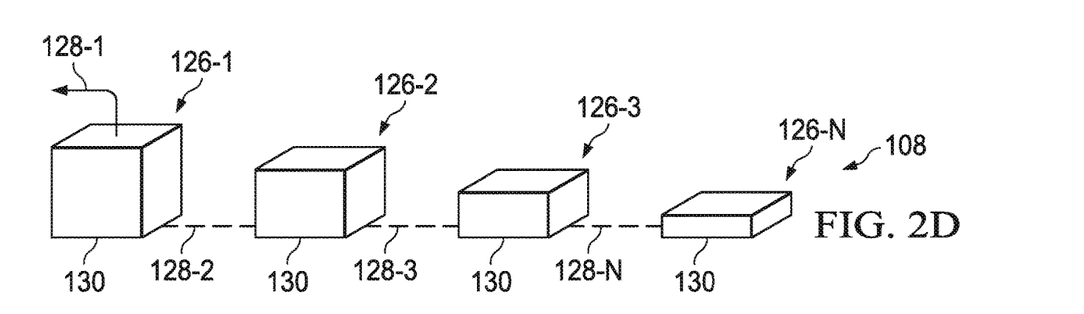

FIG. 1 is a simplified functional block diagram of an example embodiment of a therapy system 100 that can provide therapy with negative-pressure in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A tissue site may additionally include intact skin that may benefit from manipulating subcutaneous fluid movement within the lymphatic, venous, arterial, or interstitial fluid compartments.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108. In some embodiments, the cover 106 may encapsulate the tissue interface, preventing direct contact between the tissue interface 108 and a tissue site. A regulator or a controller, such as a controller 110, may also be coupled to the negative-pressure source 104.

In some embodiments, a dressing interface may facilitate coupling the negative-pressure source 104 to the dressing 102. For example, such a dressing interface may be a T.R.A.C.® Pad or Sensa T.R.A.C.® Pad available from KCI of San Antonio, Tex. The therapy system 100 may optionally include a fluid container, such as a container 112, coupled to the dressing 102 and to the negative-pressure source 104.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122, or both, coupled to the controller 110. The pressure sensor 120 may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site in some embodiments. If the tissue site is a wound, for example, the tissue interface 108 may partially or completely fill the wound, or may be placed over the wound. In other examples, a barrier or contact layer may be disposed between the tissue interface 108 and the tissue site. For example, in some embodiments, the cover 106 may encapsulate the tissue interface 108, which can reduce irritation of the tissue site. A tacky or non-irritating adhesive layer may also be applied to a surface of the tissue interface 108 in some embodiments, which can reduce irritation and hold the tissue interface 108 in place. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial bather and protection from physical trauma. For example, the cover 106 may provide a non-porous contact layer between the tissue interface 108 and a tissue site to reduce trauma to epidermis. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative-pressure can be constant, variable, intermittent, or combinations thereof according to prescribed therapeutic requirements. Negative pressure applied across the tissue site through the tissue interface 108 in the sealed therapeutic environment can induce macrostrain and microstrain in the tissue site, as well as remove exudates and other fluids from the tissue site, which can be collected in container 112.

Some embodiments of the therapy system 100 can also promote fluid propagation in a tissue site. For example, as illustrated in FIGS. 2A-2D, in some embodiments of the therapy system 100, the tissue interface 108 may comprise a sequence of foam or other manifold segments 126-1, 126-2, . . . , and 126-N (collectively, manifold segments 126), where N is an integer greater than zero. The manifold segments 126 may be fluidly coupled in sequence through restrictive fluid communication points. The communication points may be coupled with fluid conductors that substantially reduce, constrict, or otherwise limit the rate of fluid flow from one segment to another. The rate of fluid flow through the communication points is preferably limited sufficiently so that a pressure reduction can cause the manifold segments 126 to collapse in sequence. The rate limit may be dependent upon the size and structural properties of each of the manifold segments 126. For example, a tube having an internal diameter of 0.01 inches or smaller may be suitable as a fluid conductor for connecting manifold segments in some embodiments of the therapy system 100. In the example embodiment of FIGS. 2A-2D, the manifold segments 126 are interconnected by tubes 128-1, 128-2, . . . , and 128-N (collectively, tubes 128). In particular, the manifold segment 126-1 may be fluidly coupled to the manifold segment 126-2 by the tube 128-2, the manifold segment 126-2 may be fluidly coupled to the manifold segment 126-3 by the tube 128-3, and the manifold segment 126-3 may be fluidly coupled to the manifold segment 126-N by the tube 128-N. At least one of the manifold segments 126 is connected, either directly or indirectly, to the negative-pressure source 104 by the tube 128-1.

Figure 3A:
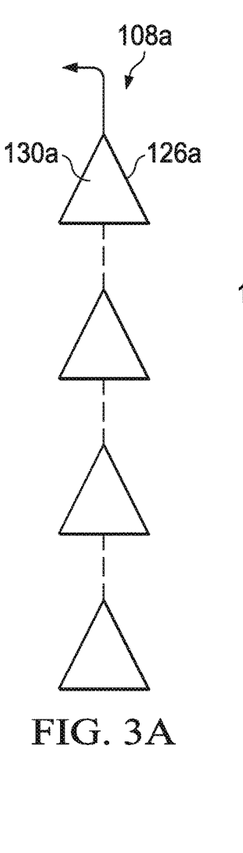
FIGS. 3A-3D are schematic diagrams of other tissue interfaces of the therapy system of FIG. 1.
Figure 3B:
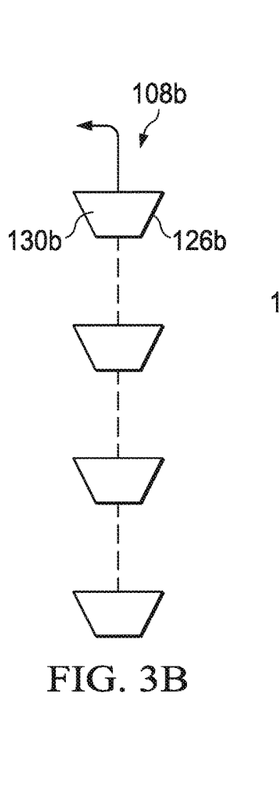
Figures 3C, 3D:
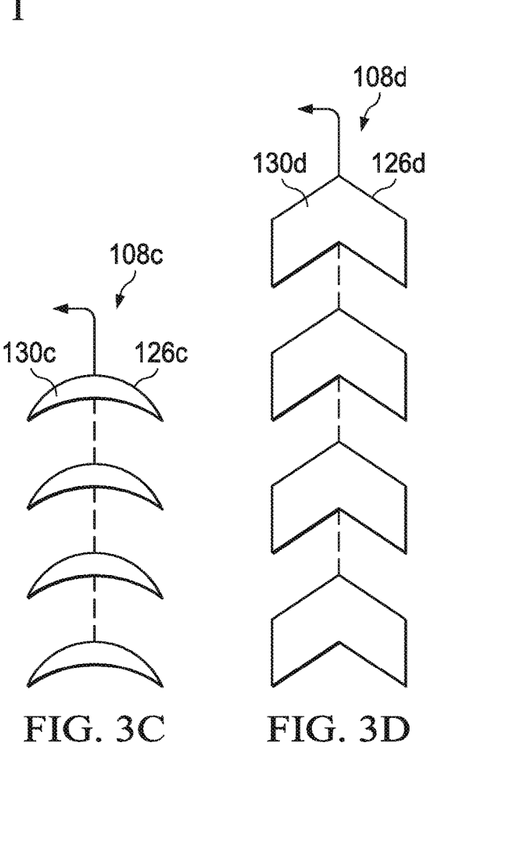

Each manifold segment 126 generally includes at least one surface adapted to engage a tissue site. For example, each manifold segment 126 in the embodiment of FIGS. 2A-2D comprises a tissue-engaging surface, illustrated as a manifold face 130. While the manifold face 130 of the manifold segments 126 illustrated in FIGS. 2A-2D is illustrated as having a generally rectangular shape, the manifold face 130 may have other shapes. For example, as illustrated in FIG. 3A, in some configurations, a tissue interface 108a of the therapy system 100 may include one or more manifold segments 126a having a triangular manifold face 130a. As illustrated in FIG. 3B, in other configurations, a tissue interface 108b of the therapy system 100 may include one or more manifold segments 126b having a trapezoidal manifold face 130b. As illustrated in FIG. 3C, in yet other configurations, a tissue interface 108c of the therapy system 100 may include one or more manifold segments 126c having a crescent manifold face 130c. As illustrated in FIG. 3D, in yet other configurations, a tissue interface 108d of the therapy system 100 may include one or more manifold segments 126d having a chevron manifold face 130d.

In general, the configurations illustrated in FIGS. 2A-3D can be used to implement sequentially-collapsing embodiments of the tissue interface 108 that can impart a waveform response within intact skin or a closed incision, and underlying tissue. During operation, for example, negative pressure applied to the tissue interface 108 can be distributed through the manifold segments 126 and the tubes 128. The constricted fluid path of the tubes 128 can impart rolling negative pressures P-1, P-2, . . . , and P-N on the segments 126-1, 126-2, . . . 126-N, respectively. The negative pressure applied to the tissue interface 108 may be constant, dynamic, or intermittent in some embodiments. For example, in some embodiments, the negative-pressure source 104 may be configured to apply a prescribed negative pressure therapy, which may comprise a sequence of several modes of operation, which can be repeated, combined, or varied over one or more time intervals. A prescribe therapy may also comprise a continuous negative pressure with periodic.

Figure 4A:
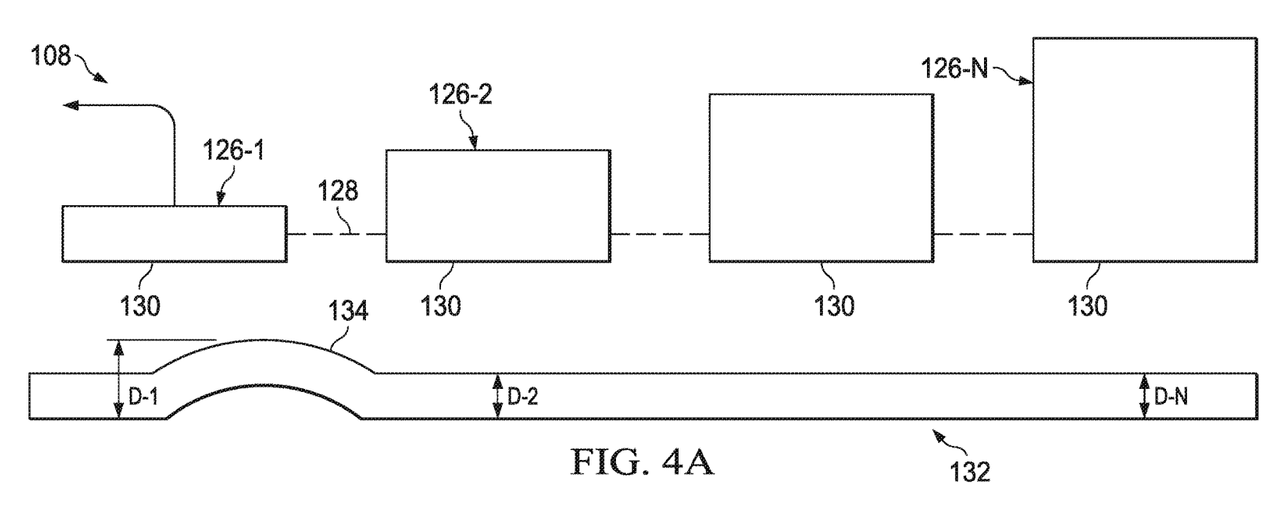
FIGS. 4A-4C are schematic environmental views of the tissue interfaces of FIGS. 2A-3D.
Figure 4B:
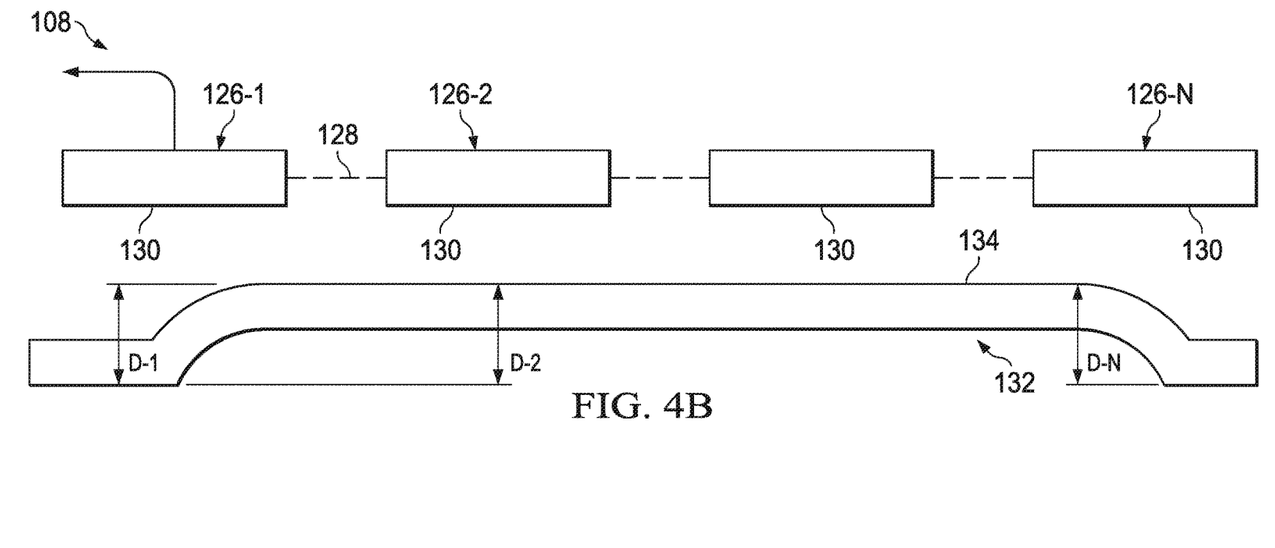
Figure 4C:
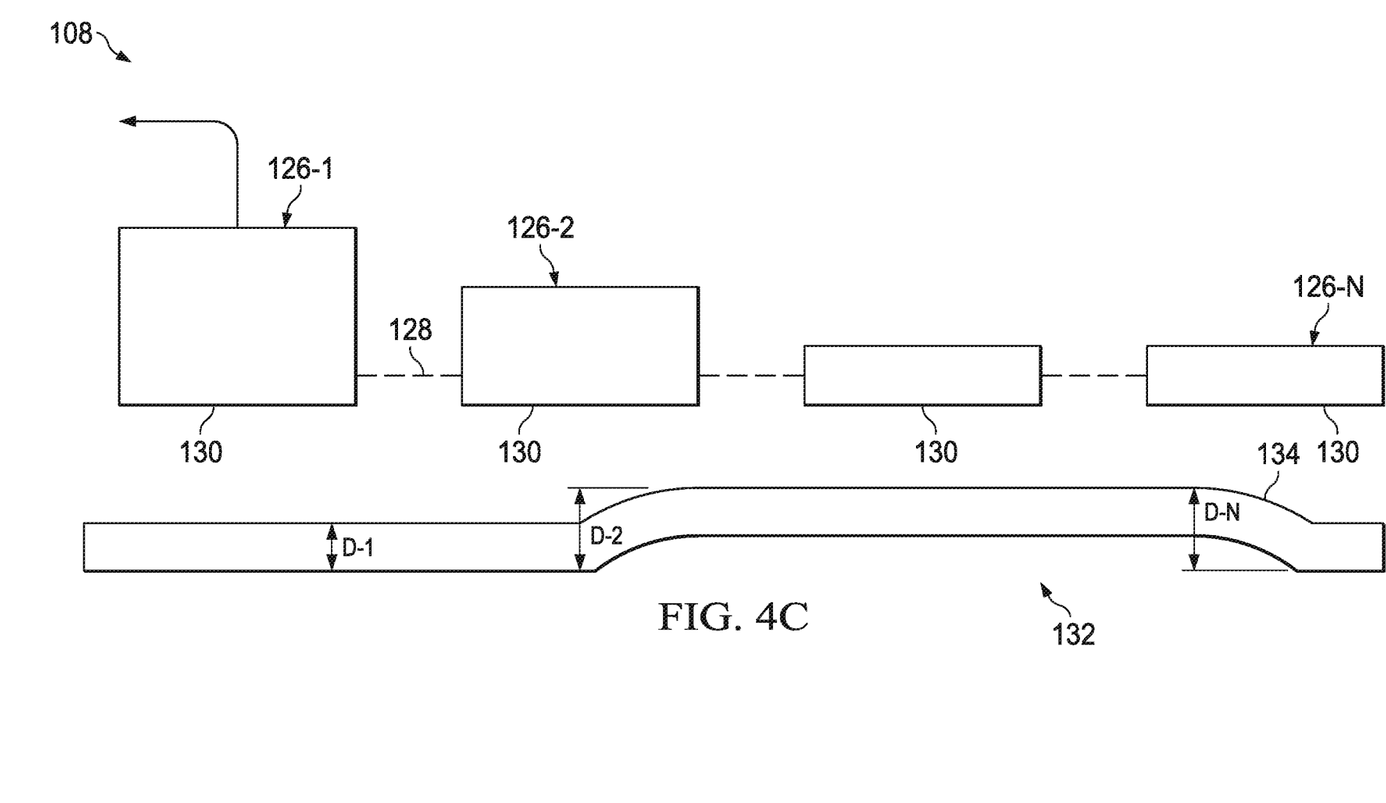

FIGS. 4A-4C schematically illustrate effects of an example therapy sequence that may be associated with some embodiments of the therapy system 100. For example, in some embodiments, the controller 110 may be programmed or otherwise configured to operate the negative-pressure source 104 in a first mode to increase negative pressure in the tissue interface 108, in a second mode to maintain negative pressure in the tissue interface 108, and a third mode to decrease negative pressure in the tissue interface 108. For purposes of illustration, a time interval during which the negative-pressure source 104 may be operated to increase negative pressure in the tissue interface 108 may be referred to herein as a "drawdown" interval. A time interval during which negative pressure in the tissue interface 108 may be maintained (within prescribed tolerances) may be referred to herein as a "holding" interval, and a time interval during which negative pressure in the tissue interface 108 may be decreased may be referred to herein as a "release" interval. Each of the time intervals may be fixed intervals, or may vary based on operating parameters, for example.

In some example embodiments, negative-pressure may be applied to the tissue interface 108 to propagate a waveform 134 in the underlying tissue 132, as shown in FIG. 4A, FIG. 4B, and FIG. 4C. For example, the controller 110 may be programmed or otherwise configured to operate the negative-pressure source 104 to apply negative pressure in a therapy sequence comprising a drawdown interval, a holding interval, and a release interval. During the drawdown interval, the waveform 134 may be propagated upstream, as illustrated in the example of FIG. 4A, and during the release interval, the waveform 134 may be propagated downstream, as illustrated in the example of FIG. 4C.

In some applications, for example, the controller 110 may operate the negative-pressure source 104 to apply negative pressure for a drawdown interval until pressure in each of the manifold segments reaches a prescribed therapy pressure. The controller 110 may then operate the negative-pressure source 104 to maintain the negative pressure for a prescribed holding interval in some embodiments. Additionally or alternatively, in some embodiments, the controller 110 may operate the negative-pressure source 104 to decrease the negative pressure for a release interval. In some embodiments, the sequence may be repeated immediately or intermittently.

In this regard, a portion of underlying tissue 132 (e.g., skin) can be lifted by negative-pressure through the manifold segments 126. For example, as illustrated in FIG. 4A, a portion of the tissue 132 aligned with the segment 126-1 can be lifted or otherwise stretched a distance D-1, while a portion of the underlying tissue 132 aligned with segment 126-2 may be lifted by a distance D-2. The distance D1 and the distance D2 may vary, but lift of 1-2 millimeters may be appropriate for some applications. Lift may be synonymous with microstrain in some applications, but may be increased by channels or other macroscopic features in the manifold segments 126, such as features illustrated in FIGS. 5-7, for example.

FIG. 4A illustrates details that may be associated with the tissue interface 108 during an example drawdown interval. During a drawdown interval, negative pressure may be applied to the tissue interface 108 for a predetermined time interval or until pressure in each of the manifold segments 126 reaches a prescribed therapy pressure, for example. As illustrated in the example of FIG. 4A, the constricted fluid path of the tubes 128 can limit the distribution rate of negative pressure through the manifold segments 126. Negative pressure may sequentially increase from the manifold segment 126-1 to the manifold segment 126-N, and the distance D-1 may initially be greater than the distance D-2, as illustrated in the example of FIG. 4A.

The lift of the tissue 132 proximate to each manifold segment 126 can increase sequentially as negative pressure increases sequentially in upstream manifold segments 126. In some applications, the tissue 132 can be lifted in sequence along the length of the tissue interface 108 by a corresponding increase of negative pressure in each subsequent manifold segment 126, and the lift of the tissue 132 proximate to each manifold segment 126 may be substantially equal at the end of a drawdown interval.

FIG. 4B illustrates details that may be associated with the tissue interface 108 during an example holding interval. During a holding interval, negative pressure in each of the manifold segments 126 may be held substantially equal, preferably at a prescribed therapy pressure. The lift distance D-1, D-2, . . . D-N of the tissue 132 proximate to each manifold segment 126 may be substantially equal during a holding interval, as illustrated in the example of FIG. 4B.

FIG. 4C illustrates details that may be associated with the tissue interface 108 during an example release interval. During a release interval, negative pressure in the tissue interface 108 can be decreased for a predetermined time interval, or until pressure in each of the manifold segments 126 reaches atmospheric pressure or another prescribed therapy pressure, for example. In some embodiments, negative pressure from the negative-pressure source 104 may be decreased, or negative-pressure may be vented, for example. As illustrated in the example of FIG. 4C, the tubes 128 or another constricted fluid path can limit the rate of decrease in manifold segments 126 during a release interval. For example, during a release interval, negative pressure may sequentially decrease from the manifold segment 126-1 to the manifold segment 126-N, so that negative pressure P-1 may initially be less than to negative pressure P-2 during a release interval. During a release interval, the distance D-1 may also be less than or equal to the distance D-2 and/or D-N, as further illustrated in the example of FIG. 4C.

Figure 5:
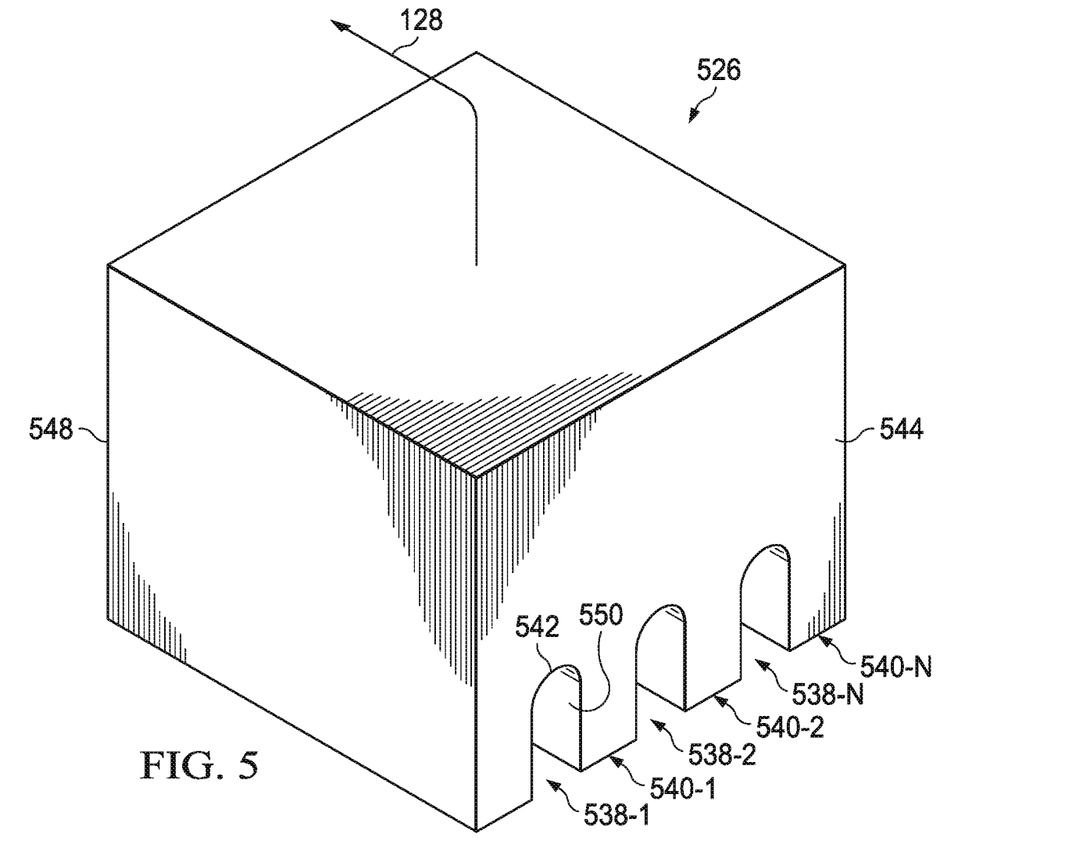
FIG. 5 is a perspective view of a manifold segment of the tissue interface of FIGS. 2A-3D.
Figure 6:
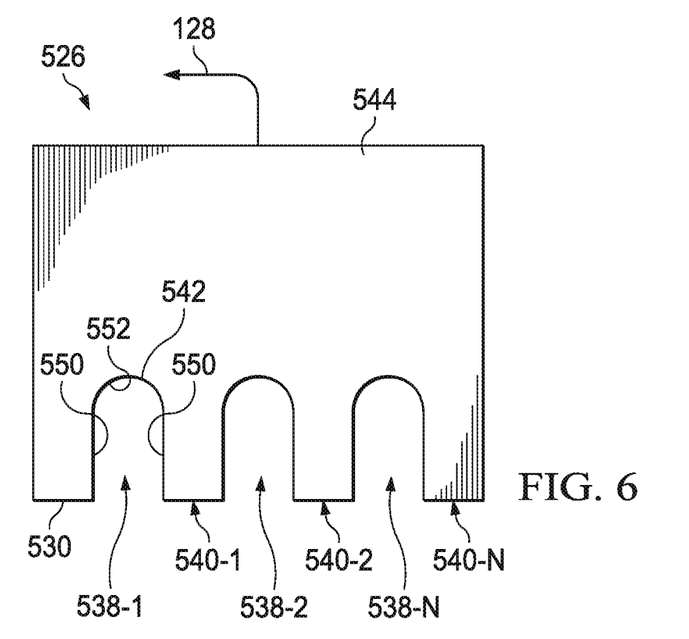
FIG. 6 is a front elevation view of the manifold segment of FIG. 5.
Figure 7:
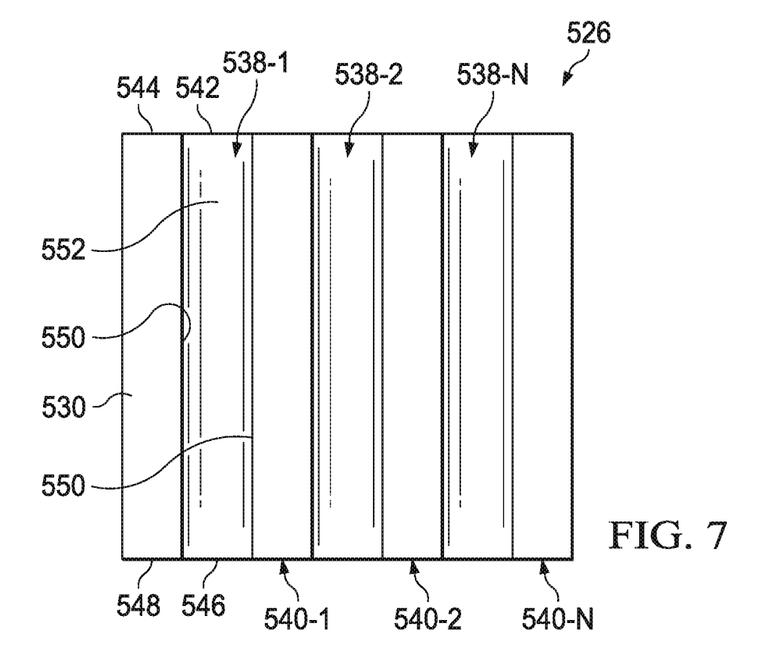
FIG. 7 is a bottom view of the manifold segment of FIG. 5.

Referring now to FIGS. 5-7, an example configuration of a manifold segment 526 is shown. The manifold segment 526 may be associated with some example embodiments of the therapy system 100. The manifold segment 526 may include a manifold face 530 having a sequence of voids 538-1, 538-2, . . . , and 538-N (collectively, voids 538). The voids 538 are preferably distinct from pores or other fluid pathways of the manifold segment 526. For example, while the manifold segment 526 may comprise a porous foam in some embodiments, the voids 538 are typically at least an order of magnitude larger than pores of the foam. For example, in some embodiments, the voids 538 may have a depth of 0.5-10 millimeters, but generally vary depending upon the stiffness of the material of the manifold segment 526. A stiffer material may require less depth than a more collapsible material to impart corresponding stretch in the tissue. Additionally or alternatively, the voids 538 generally define macroscopic surface features adapted to impart an elastic stretch on tissue under negative-pressure. For example, in some configurations, the voids 538 may be disposed in a pattern on the manifold face 530 of the manifold segment 526 to define ridges 540-1, 540-2, . . . , and 540-N (collectively, ridges 540). As shown in FIGS. 5-7, in some configurations the manifold face 530 may include an alternating pattern of voids 538 and ridges 540. The voids 538 may form a pattern of discrete islands in some embodiments. The voids 538 may have a rounded cross-section, a square cross-section, or a combination of cross-section shapes, for example. In some embodiments, the voids 538 and/or ridges 540 may extend in a direction parallel to one another, defining one or more channels or grooves in the manifold face 530. For example, in the embodiment of FIGS. 5-7, each void 538 may include a first opening 542 in a first side 544 of the manifold segment 526, and a second opening 546 in a second side 548 of the manifold segment 526. The void 538 may be defined by a pair of opposing sidewalls 550 and an upper wall 552 extending from and between the first sides 544 and the second sides 548 of the manifold segment 526. The sidewalls 550 may extend in a direction parallel to each other, and perpendicular to the manifold face 530. In some configurations, the upper wall 552 may be concave.

Figure 8:
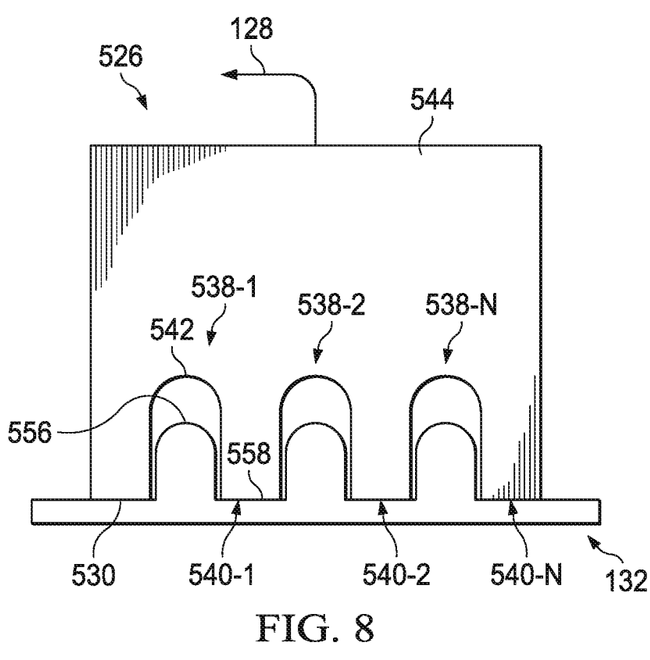
FIG. 8 is a schematic environmental view of the manifold segment of FIG. 5.

In general, the configuration illustrated in FIGS. 5-7 can be used to stretch the underlying tissue 132 relative to the manifold face 530 of the manifold segment 526. For example, as illustrated in FIG. 8, during operation, negative pressure applied to the tube 128 can impart negative pressure P to the manifold segment 526. As negative pressure P is applied to the manifold segment 526, the tissue 132 aligned with the manifold segment 526 may be drawn into engagement with the manifold face 530. Portions 556 of the tissue 132 aligned with the voids 538 may be lifted or otherwise drawn into the voids 538, such that the portions 556 are elevated and stretched relative to portions 558 aligned with the ridges 540.

The systems, apparatuses, and methods described herein may provide significant advantages. For example, an interconnected sequence of manifolds or manifold segments and restrictive fluid conductors can help to propagate a waveform in tissue. Such a waveform may promote or facilitate drainage, flow, or movement of interstitial, lymphatic, and/or vascular fluid in underlying tissue, and can also provide a massaging effect. Removal of fluid from tissue can aid in the healing of wounds. For example, during a drawdown mode of operation, a waveform can direct the flow of fluid in a first direction, and a release mode of operation can direct the flow of fluid in a second direction. Additionally or alternatively, voids in a face of the manifolds can stretch and lift underlying tissue, and thereby aid in the healing of wounds. A waveform therapy may also be used to move fluid away from a closed incision site, move fluid through the lymphatic system in cases of lymphedema or excessive fluid accumulation, or facilitate venous return in compromised patients, and may be beneficial for subcutaneous seroma management.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for treating a tissue site, the system comprising:
    a negative-pressure source;
    manifold segments sequentially connected to the negative-pressure source, each of the manifold segments being formed from foam and attached to another of the manifold segments through a tube, the tube configured to constrict flow between the manifold segments; and
    a controller operatively coupled to the negative-pressure source;
    wherein the controller is configured to operate the negative-pressure source to apply negative pressure to each of the manifold segments such that the manifold segments collapse in a wave pattern.

2. The system of claim 1, wherein each manifold segment includes a manifold face having a void depending into the manifold face and adapted to draw tissue into the manifold segment.

3. The system of claim 2, wherein the void includes a first opening formed in a first side of each manifold segment, and a second opening formed in a second side of each manifold segment.

4. The system of claim 1, wherein each manifold segment includes a manifold face having a first void, a second void, and a ridge formed between the first void and the second void.

5. The system of claim 4, wherein the first void is parallel to the second void.

\* \* \* \* \*